United States Patent [19]

Borodic

[11] Patent Number: 5,298,019
[45] Date of Patent: * Mar. 29, 1994

[54] CONTROLLED ADMINISTRATION OF CHEMODENERVATING PHARMACEUTICALS

[75] Inventor: Gary E. Borodic, Canton, Mass.

[73] Assignee: Associated Synapse Biologics, Boston, Mass.

[*] Notice: The portion of the term of this patent subsequent to Feb. 2, 2010 has been disclaimed.

[21] Appl. No.: 4,090

[22] Filed: Jan. 13, 1993

Related U.S. Application Data

[63] Continuation of Ser. No. 570,395, Aug. 21, 1990, Pat. No. 5,183,462.

[51] Int. Cl.$^5$ .............................................. A61M 31/00
[52] U.S. Cl. ...................................... 604/51; 128/898
[58] Field of Search ................................... 604/49-53, 604/28; 128/749, 898, 632, 635, DIG. 13; 514/903

[56] References Cited

U.S. PATENT DOCUMENTS

| | | |
|---|---|---|
| 2,979,055 | 4/1961 | de Beer et al. |
| 3,898,983 | 8/1975 | Elam |
| 4,331,145 | 5/1982 | Winter |
| 4,445,515 | 5/1984 | DiResta |
| 4,501,582 | 2/1985 | Schulz |
| 4,522,302 | 6/1985 | Paikoff |
| 4,664,911 | 5/1987 | Uhr et al. |
| 4,810,243 | 3/1989 | Howson |
| 4,880,014 | 11/1989 | Zarowitz et al. |
| 4,932,936 | 6/1990 | Dykstra et al. |
| 5,053,005 | 10/1991 | Borodic |
| 5,097,834 | 3/1992 | Skrabal |
| 5,183,462 | 2/1993 | Borodic ........................ 604/51 |

OTHER PUBLICATIONS

Blitzer, "Botulinum Toxin Injection For The Treatment Of Oromandibular Dystonia", Presented at Meeting of the American Laryngological Association, (1988).
Borodic, "Botulinum A Toxin For The Treatment Of Spasmodic Torticollis: Dysphagia and Regional Toxin Spread", Head & Neck, (1990).
Borodic, "Dose-Response Relationships in Patients Treated With Botulinum Toxin for More Than Three Years", Ear, Nose and Throat, 67:914 (1988).
Borodic, "Blepharospasm and Its Treatment, with Emphasis On The Use Of Botulinum Toxin", Plastic and Reconstructive Surgery, (1989).
Borodic, "Innervation Zone Of Orbicularis Oculi Muscle And Implications For Botulinum A Toxin Therapy", Ophthalmic Plastic and Reconstructive Surgery, 7(1):54-60 (1991).
Brown, "The Role of Dietary Carbohydrates in Plaque Formation and Oral Disease", Nutrition Reviews, 33:353-361 (1975).
Das, "Effect of Treatment With Botulinum Toxin On Spasticity", Postgraduate Medical, 65:208-210 (1989).
Das, "Botulinum Toxin In Treating Spasticity", BJCP, 43:401-403.
Dunlop, "Neuroscience Applied To Clinical Problems Botulinum-A Toxin Used For Chemodenervation of Muscles in Spasm", (Abstract).

(List continued on next page.)

Primary Examiner—Vincent Millin
Assistant Examiner—Sebastiano Passaniti
Attorney, Agent, or Firm—Testa, Hurwitz & Thibeault

[57] ABSTRACT

This invention relates to a method for controlled administration of chemodernervating agents such as botulinum toxin-derived pharmaceutical, useful in attenuating neural stimulation and spasmodic activity of muscle. The method involves administration of novel dosage forms based upon the standardization of denervating pharmaceuticals. The invention also relates to novel methods of administrating chemodernervating agents in a controlled and reproducible manner so as to confine their effects to a given region of muscle mass while minimizing in adjacent muscle tissue.

3 Claims, 1 Drawing Sheet

OTHER PUBLICATIONS

Evans, "Botulinum Neurotixin Type B Its Purification, Radioiodination And Interaction with Rat-Brain Synaptosomal Membranes", *Eur. J. Biochem.*, 154:409-416 (1986).

Gelb, "Controlled Trial Of Botulinum Toxin Injections in the Treatment Of Spasmodic Torticollis", *Neurology*, 39:80-84 (1989).

Gluckstein, "Clinical Use Of Botulinum Toxin", *Current Bibliographies In Medicine*, Jan. 1987-Sep. 1990.

Gonnering, "Negative Antibody Response to Long-Term Treatment Of Facial Spasm With Botulinum Toxin", *American J of Ophthalmology*, 105:313-315 (1988).

Jankovic, "Botulinum A Toxin For Cranial-Cervical Dystonia: A Double-Blind, Placebo-Controlled Study", *Neurology*, 37:616-623 (1987).

Ludlow, "Spasmodic Dysphonia: Botulinum Toxin Injection After Recurrent Nerve Surgery", *Otolaryngol Head Neck Surg.*, 102:122-131 (1990).

Singh, "Molecular Topography And Secondary Structure Comparisons Of Botulinum Neurotoxin Types A, B and E", *Molecular and Cellular Biochemistry*, 86:87-95 (1989).

Snow, "Treatment of Spasticity With Botulinum Toxin: A Double-Blind Study", *Annals of Neurology*, 28:512-515 (1990).

Tsui, "Production of Circulating Antibodies To Botulinum-A Toxin In Patients Receiving Repeated Injections For Dystonia", (Abstract).

Tsui, "A Pilot Study On The Use Of Botulinum Toxin In Spasmodic Torticollis", *Can. J. of Neurological Sciences*, 12:314-316 (1985).

Tsui, "Local Treatment Of Spasmodic Torticolli With Botulinum Toxin", Can. J. Neurol. Sci., 14:533-535 (1987).

VanZandijcke, "Treatment of Bruxism With Botulinum Toxin Injections", *J. Neurol., Neurosurg., Psychiatry*, 53:530 (1990).

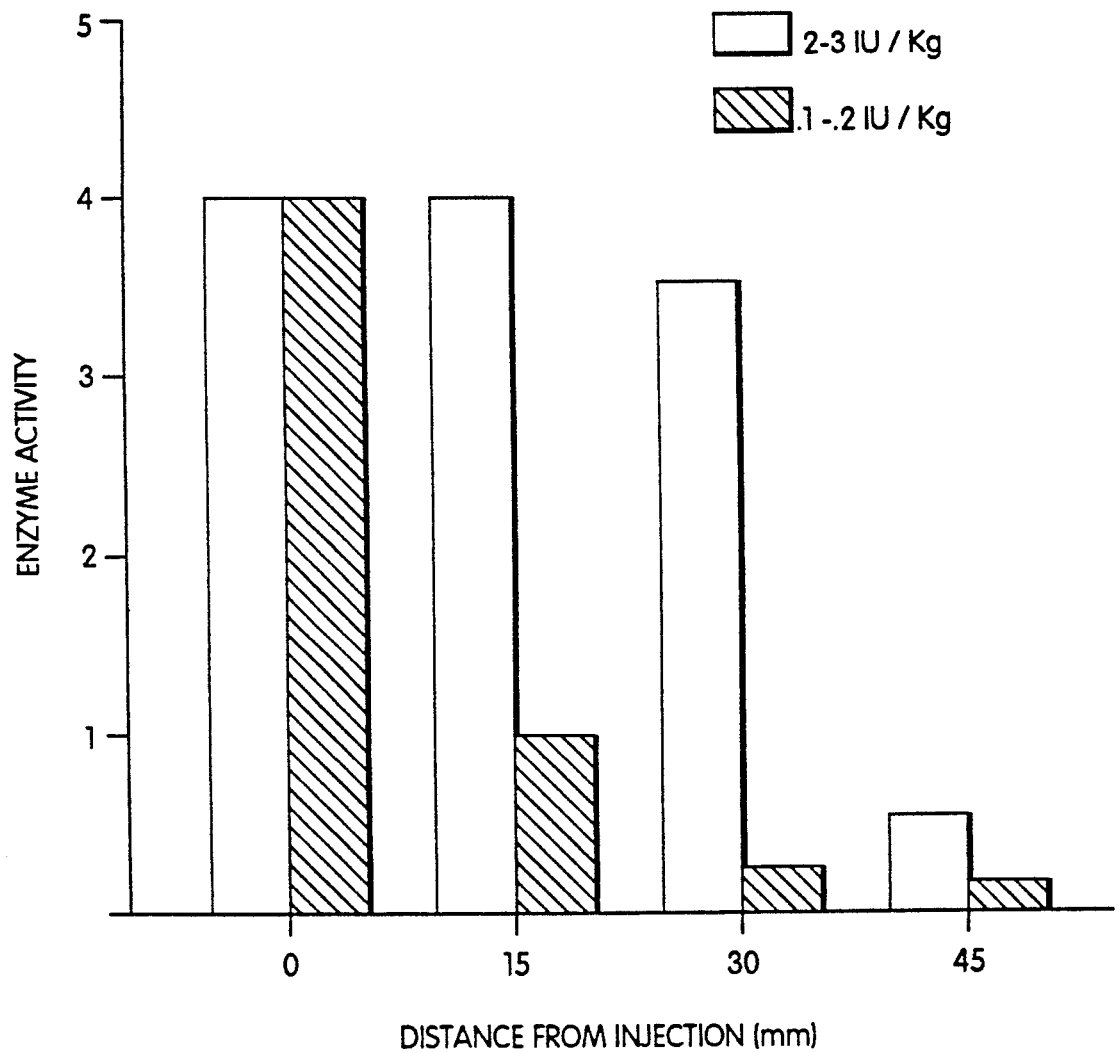

CONTROLLED ADMINISTRATION OF CHEMODENERVATING PHARMACEUTICALS

This is a continuation of copending application Ser. No. 07/570,395 filed on Aug. 21, 1990, now U.S. Pat. No. 5,183,462.

BACKGROUND OF THE INVENTION

This invention relates to controlled administration of chemodernervating agents, e.g., botulinum toxin-derived pharmaceuticals, useful in attenuating neural stimulation and spasmotic activity of muscle. More particularly, the invention relates to a method of standardizing denervating pharmaceuticals and novel dosage forms based thereon which permit medically safe administration in the management of a variety of diseased states and injuries characterized by involuntary muscle spasm or hyperactivation. The invention also relates to novel methods of administering chemodenervating agents in a controlled and reproducible manner so as to confine their effect to a given region of muscle mass while minimizing paresis in adjacent muscle tissue.

Pharmaceutical grade preparations from the toxin produced by *Clostridium botulinum* have been available for many years from Dr. Allan Scott and the Kettlewell Ophthamology Institute of San Francisco, Calif., and now is sold commercially by Allergan Pharmaceuticals, Inc. Many other materials toxic to neuromuscular transmission are known, such as tetanus toxin and various subtypes of botulinum toxin. Botulinum toxin preparations recently have been approved for the treatment of blepharospasm and strabismus, and clinical trials are underway on the treatment of spasmodic torticollis. Dykstra et al have proposed in U.S. Pat. No. 4,932,936 that botulinum toxin can be used in the treatment of spasmodic sphincter muscle which leads to urinary incontinence ("neurogenic bladder") characteristic of some forms of cancer. A survey of the literature provides evidence for the potential use of chemodenervating agents such as botulinum toxin in the treatment of other significant spasmodic diseases including jaw dystonias, occupational dystonias, corneal ulceration (protective ptosis), spasmodic dysphonia, and various forms of facial dyskinesis including Meige syndrome, hemifacial spasm, aberrant regeneration of facial nerves, and apraxia of eyelid opening.

Treatment of these diseases involves injection of a chemodenervating agent, currently a botulinum preparation, directly into the muscle, using, for example, a fine gage teflon-coated needle under electromyographic control to aid the physician in locating the intended intramuscular locus of the injection. The pure active toxin is believed to be the single most toxic material known. A sufficient dose of the toxin acts on striated muscle to block release of the acetylcholine neurotransmitter from the presynaptic membrane resulting in varying degrees of effective denervation of the muscle in regions contacted by the toxin. This results in an increase in post-synaptic acetylcholinesterase activity and an increase in the population of acetylcholine receptors, effects which occur as a characteristic physiological response to denervation. After a period of days, the axon terminals develop sprouting, and over a period of several months, collateral motor axons establish new neuromuscular connections with the muscle fiber. As neuromuscular junctions are regenerated, full function of the muscle returns along with the spasmodic contractions or hyperstimulation symptomatic of the disease.

With the exception of the emerging spasmodic torticollis therapy, development of the therapeutic uses of botulinum toxin preparations has been limited to small muscles which may be treated with lower doses and have limited risk of toxin spread. Development of the therapies has proceeded empirically using low doses without theoretical basis or clinical data predictive of the distribution of the toxin in vivo. Currently, toxin preparations are quantified by measuring the $LD_{50}$ in white mice. $LD_{50}$ in white mouse equals one international unit or I.U.

The treatment of blepharospasm with botulinum toxin as disclosed by Borodic et al in *Plastic and Reconstructive Surgery*, (March, 1989) is illustrative of a protocol for use of the toxin. Generally, for bilateral blepharospasm, a starting dose totalling 10 to 20 IU is injected at 4 to 6 sites in the upper and lower eyelid of each eye spaced laterally from the midline of the lid and close to the lash base of the upper lid. Injections above the brow are given only if significant involuntary movements are recurring in this region. If the toxin is injected too close to the upper lid fold, diffusion through the orbital septum can weaken the levator palpebrial superioris muscle and induce ptosis. If the toxin is injected too medially in the lower lid, the naso-lacrimal pumping mechanism can be weakened excessively resulting in epiphora. With an appropriate dose, because the muscle is only partially weakened, enough strength and neural control remain so that a treated muscle still can perform its primary voluntary function. The degree of weakening from denervation can be "titrated" empirically for particular patients by altering the dose.

SUMMARY OF THE INVENTION

This invention provides a novel method of measuring the activity of neurotoxin derived chemodenervation pharmaceutical preparations, such as botulinum toxin-derived preparations. Exploitation of the method permits manufacture of the preparation in standardized dose forms of predictable clinical effect labeled to indicate the zone of denervation activity that will be induced by a unit dose of the preparation when injetted in vivo. Provision of such dosage forms and the teaching disclosed herein permits the physician to preselect appropriate dosage in advance of injection of the preparation and to chemodenervate a given volume of muscle mass while essentially confining diffusive spread of the toxin within that predetermined volume. Thus, practice of the method of the invention permits the physician to avoid or minimize the complications of therapies involving such agents, i.e., to avoid inducing unwanted dysphagia or partial paralysis in muscles adjacent the site of injection which may be directly or indirectly life threatening, incapacitating, or disfiguring. Practice of the invention permits more exacting application of the toxin and facilitates its use in large muscle groups of the limbs and trunk.

The foregoing is accomplished by determining experimentally within a muscle of an experimental animal the spatial extent of inhibition of acetylcholine release about a site of injection of a unit quantity of the preparation. The determination may be made in several ways. One can determine the extent of inhibition of muscle stimulation in regions spaced apart from the site of injection by electrophysiologic testing, for example, electromyography, e.g., single fiber electromyography. This method of determining the spatial extent of inhibition of acetylcholine release is most direct but also most cumbersome. More easily conducted indirect measurements currently are preferred. These techniques involve postmortem sectioning of muscle at regions spaced apart from the site of injection and determining the extent of denervation by indirect methods which take advantage of the known physiologic effects of neurotoxin based chemodenervation phenomena. For example, one may employ suitably labeled monoclonal antibody or polyclonal antisera raised against an epitope or epitopes of the toxin preparation which remain exposed or becomes exposed upon binding of the toxin to the motor end plate, against acetylcholine receptors (which increase significantly in response to denervation), or against acetylcholinesterase (which also increases upon denervation). The currently preferred method is to determine the local concentration of acetylcholinesterase in regions of the muscle spaced apart from the site of injection by colorimetric estimation of enzyme activity.

Practice of the invention permits manufacture of novel dosage forms which are safer to administer, and permits expansion of chemodenervation therapies to the management of diseased states in larger muscles and muscle groups while reducing the risk of side effects. Thus, in another aspect, the invention comprises a novel article of manufacture comprising a package containing a neurotoxin-derived pharmaceutical for chemically inducing in vivo, upon injection of a unit dose of the pharmaceutical into a point in a muscle, at least partial denervation in a predetermined volume of muscle tissue spaced about the injection point. Printed on the label for the package or as an insert is information indicative of the volume of in vivo activity of a unit dose of the pharmaceutical. The physician thus can purchase, for example, a pharmaceutical preparation known in advance to induce partial chemodenervation within, for example, 3 mm, 10 mm, or 30 mm about the site of injection.

With knowledge of the gross or microscopic anatomy of the muscle or muscle group involved, the physcian can chemically denervate reproducibly a preselected volume of muscle tissue without inducing significant paresis in muscle tissue outside the preselected volume. This may be accomplished by selecting a particular unit dosage form and injecting a unit dose in one, or more typically in a number of spaced apart locations within the muscle to induce denervation within the preselected volume. The physician therefore can more clearly estimate the depth and area of toxin spread.

The exact form of the dose of a pharmaceutical standarized in accordance with the invention can vary. Thus, the pharmaceutial may be lyophilized and in condition to be reconstituted before use, or may comprise a stabilized protein solution. While the invention is unlimited with respect to the nature of the neurotoxin which is standardized, it preferably is practiced on biologicals produced by prokaryotes such as those from the genus Clostridium. The currently most preferred neurotoxin is a botulinum toxin-derived pharmaceutical, most preferably a preparation derived from botulinum toxin type A. It may however take the form of any of the known types of botulinum toxin (A through G) or various engineered proteins which retain the native form's ability to block acetylcholine release.

Knowledge of the in vivo biodistribution of chemodenervating agents gained by the practice of the invention permits very significant expansion of the use of these materials in the management of human disease. The agents may be used safely either for their direct or indirect effects. One example of their indirect effects involves use of such materials in facial cosmetic applications. The administration of an appropriate dose of, for example, botulinum toxin, to attenuate tone of muscles about the eyes and forehead can in many cases remove wrinkles characteric of aging in skin overlying the muscle while inducing only mild, often acceptable muscle weakness. Such chemodenervating agents also may be used to induce cosmetic improvement in hemifacial paralysis by intentionally inducing partial paralysis in the contralateral side of the face thereby to improve bilateral facial symmetry. The materials may be injected at points spaced asymetrically about the spine within paraspinal muscles to alter muscular support for the spine in juveniles to prevent or ameliorate the development of scoliosis. Injection of low doses of the agents into muscles activating the jaw can retard tooth wear caused by involuntary or unconscious clenching of the teeth.

Examples of direct effects are the treatment of unwanted involuntary pathologic muscle stimulation, i.e., spasm, rigidity, or hyperstimulation, by direct injection throughout, or in the area of innervation of, the affected muscle or muscles. Thus, diseases involving muscle spasticity in general can be treated, typically without regard for its cause. The drug may be used to alleviate overstimulation, rigidity, or spasticity in muscle or muscle groups caused by stroke, cerebral palsey, multiple sclerosis, unilateral or bilateral parkinsonism, and other diseases characterized by spasmodic or continuous muscle hyperstimulation.

Accordingly, it is an object of the invention to provide a novel method of standardizing chemodenervating neurotoxin-derived pharmaceuticals such as botulinum-derived pharmaceuticals. Another object is to standardize botulinum toxin preparations with respect to their zone of denervation when injected in vivo. Another object is to provide novel dosage forms of such agents. Yet another object is to provide novel therapies for muscle spasticity and/or hyperactivation heretofore untreatable or treatable only imperfectly with systemic drugs or surgery.

BRIEF DESCRIPTION OF THE DRAWING

Other objects and features of the invention will be apparent from the description and claims which follow and from the drawing wherein the sole Figure is a bar graph illustrating measurement of the zone of chemodenervation of two botulinum toxin preparations.

DESCRIPTION

The invention may be practiced on any substance capable upon injection of interrupting nerve impulse transmission across the neuromuscular junction. While many such neurotoxins are known, the currently most promising reagents of this type are the family of toxins derived from *Clostridium botulinum*, and the most preferred is pharmaceutical grade botulinum toxin Type A available commercially from Allergan Pharmaceuticals, Inc. under the tradename OCULINUM. However, it should be stressed at the outset that it is a fundamental advantage and feature of the invention that it can be applied to any injectable substance which interrupts neuromuscular transmission at the synapse, and that other materials of this type when and if developed to pharmaceutical grade could be used in the novel therapies. Thus, it is contemplated that other materials, protein subunits, recombinantly produced materials, and other various novel types of pharmaceutical preparations can be used in the practice of the invention to advantage. However the work forming the basis of the invention was conducted using the commercially available botulinum toxin-based material identified above, and the remainder of the discussion will be limited to this material, hereinafter referred to simply as "toxin".

Injection of a sublethal dose of a toxin into muscle deposits a bolus of the material intramuscularly which diffuses outwardly to a distance that is a complex and currently unknown function of, inter alia, the identity and amount of diluent if any injected with the toxin, the mass of the toxin, the population of presynaptic receptors about the site of injection, and the then current physiological condition of the patient. Diffusion, driven presumably by the concentration gradient, slows as active toxin binds to receptors on the presynaptic membrane. Some portion of the toxin is swept away by the vascular system and distributed systemically. Some other portion may be proteolytically degraded before binding.

Doses far smaller than the $LD_{50}$ for man (believed to be on the order of 2 $\mu$g) can paralyze completely, or partially or lightly denervate a muscle volume, depending on dose. The therapeutic effects are achieved at dosage levels in the range between a few I.U. to 500 to 1000 I.U., preferably no more than 500 I.U., and most preferably no more than 300 I.U., administered as a plurality of injections about a muscle or muscle group. Injection of a therapeutic dose results in destruction of a subset of the neuromuscular junctions innervating the muscle but leaves others in a functional state.

It has been hypothesized that a threshold quantity of the toxin must bind to a particular axon before that axon becomes irreversibly poisoned and the denervation-renervation cycle is initiated. Motor end plates which receive a dose below the threshold presumably recover and participate together with unaffected axons in continued innervation of the muscle. Support for this model of drug action comes from the observations that: transient low level retardation of muscle stimulation can be detected in some cases in muscles remote from the site of injection; an animal poisoned intraperitoneally with the toxin upon autopsy shows no histological signs of denervation, and; there is a gradient of denervation about the site of injection. Another factor affecting dose response is the existence of innervation zones within muscles, i.e., there are differences in the microanatomical distribution of neuromuscular junctions within muscles. A literature search suggests that little is known about muscle innervation patterns. However, it is clear that some muscles are enervated more or less uniformly throughout their mass whereas others have a zone of innervation in one region. Thus, particularly in large muscles, the locus of injection within the muscle can influence the physiological response.

The extent of denervation of a muscle can be determined postmortem by sectioning the muscle and staining for acetylcholinesterase activity using the method of Karnovsky (See Woolf and Coers, *The Innervation of Muscle*, Charles Thomas Pub, Springfield, Ill., 1959). As disclosed below, excision of human muscle previously treated with the toxin, and postmortem sectioning of rabbit muscle about a site of toxin injection, exhibit a gradient of denervation akin to that disclosed by Duchen in mice (See J. Neurol. Neurosurg. 1970:33:40-54; J. Physiol. (Lond) 969; 204:17-18).

In accordance with the invention, the extent of spread of a given dose of a chemodenervating agent is used as a measure of the activity of the preparation, and is used to quantify an appropriate dose for injection into a muscle or muscle group. This permits the physician to confine the action of the toxin to a predetermined volume of muscle and to prevent or minimize the spread of the toxin into adjacent muscle tissue.

For example, a given dose of a given preparation is injected into the muscle of an experimental animal. After three to five weeks, the animal is sacrificed, and in order to assess toxin spread of the injected dose, sections are taken about the site of injection, for example, 3, 10, 15, 30, 45, and 60 mm from the site. Each of the sections is stained to determine, for example, acetylcholinesterase activity. This permits visualization of the zone of effective denervation which can be determined rather precisely. Alternatively, the muscle may be sectioned through the point of injection across the denervated field and stained so that the gradient can be observed readily. Correlation of these data between, for example, small rodents and simians by direct observation, or between the experimental animals and surgically excised human muscle, backed by clinical experience, provide precise information on the zone and extent of denervation a given dose of toxin will induce when injected at a given site in a human.

Determination of the extent and zone of inhibition of acetylcholine release can be measured by various techniques known to those skilled in the art in addition to acetylcholinesterase staining, including single fiber electromyography (See, for example, Sanders et al, *Botulinum Toxin for Blephorospasm, Single Fiber EMG Studies*, Neurology, 1985; 35:271-272) and by using labeled binding proteins such as polyclonal or monoclonal antibodies labeled with, for example, fluorescein of other fluorescent moiety, colloidal metallic particles, or other remotely detectable substance. Antibodies can be produced, using known techniques, to acetylcholine receptors or to acetylcholinesterase, both of which can serve as a marker for effective denervation, or to epitopes which are newly exposed, or which remain after binding of the toxin to the receptor on the presynaptic motor end plate. Other stains may be used such as hematoxylin, eosin, and masson trichrome. Any of these techniques and others that can be devised may be used to determine the extent of diffusion and effective denervation of a given dose of a chemodenervating agent within the muscle of an experimental animal.

Use of the technique enables chemodenervating agents to be prepared in various dosage forms and provides nomograms which enable the physician to inject the agents for therapeutic purposes in humans responsibly while eliminating or minimizing side effects caused by unwanted toxin spread beyond the intended denervation zone. Some degree of paresis and muscle weakening beyond the intended locus of denervating action may nevertheless occur. However, the physician may use the techniques and chemodenervating pharmaceuticals standardized as herein disclosed to tailor dose to the selected point or points of injection based on his diagnosis determining the affected muscles. The denervating effect therefore can be confined essentially to a given muscle or muscle groups despite the observation that botulinum toxin can spread beyond intervening facial planes and bony structures. Data obtained using the process of the invention to date indicate clearly that the size of the field of action of therapeutic injections of chemodenervating agents is dose dependent. Furthermore, several of the observed complications in established clinical protocols have been correlated to spread of the toxin beyond the intended field of action by retrospective and prospective study of the anatomic injection sites and doses.

The sole figure of the drawing is a graph disclosing data representative of the type that can be generating using the process of the invention. Longissimus dorsi muscle of groups of six New Zealand white rabbits were studied to assess differences in acetylcholinesterase staining activity at varying distances from the site of injection of two separate doses of botulinum toxin. The first dose contained four to six I.U. as determined by dilution from a 100 I.U. vial of the commercial preparation; the second contained 0.2 to 0.4 I.U. The toxin was reconstituted at 1.25 I.U. per 0.1 ml physiological saline. The point of injection was marked with a tattoo. The injections were made 5 to 8 mm deep directly into the muscle. A control animal was injected with the saline diluent. After five weeks, the animals were sacrificed, and sections of the muscle were taken 15, 30, and 45 mm caudel from the sites of injections transverse to the spine and in a direction parallel to the spine on the contralateral side. Acetylcholinesterase slide staining was conducted by placing muscle specimens in Baker's solution (10% formol-calcium), which then were refrigerated, and after 24 hours, placed in 0.88 gum sucrose for 2 to 3 hours. the muscle then was sectioned into 10 micrometer sections in a cryostat at a $-20°$ C. and placed on gelatin-coated slides. Acetylcholinesterase activity was demonstrated by Karnovsky's method, and the slides were incubated for 90 minutes at $37°$ C., washed in distilled water, counterstained with fast green, dehydrated rapidly, and mounted.

At the site of injection, diffuse acetylcholinesterase staining was seen over essentially all muscle fibers. For the larger dose, (2 to 3 I.U./kg) the muscle histology was essentially identical at 15 mm. At 30 mms, a decrease in acetylcholinesterase enzymatic activity was indicated by a reduction in color intensity, but very significant muscle denervation was still apparent. At 45 mm, a very significant reduction in enzyme activity was noted. For the smaller dose (0.1 to 0.2 I.U./kg) immediately about the site of injection enzyme activity was similar to the larger dose. However, at 15 mm from the site of injection, denervation was markedly diminished, and at 30 mm and 45 mm, enzyme activity was barely above levels observed in control specimens. Contralateral longissimus dorsi biopsy specimens revealed staining intensities similar to those observed in the specimens discussed above, illustrating that toxin diffuses unhindered through facial planes and about bone.

These results demonstrate the feasibility of the standardization process of the invention. That such results can be used to improve the clinical efficacy of botulinum preparations was demonstrated in the clinic as follows.

Retrospective reviews were conducted from the records of patients with adult onset idiopathic spasmotic torticollis who had been given botulinum A toxin for a period of two to thirty-eight months (average 1.1 years) and who had experienced the complications of dysphagia (difficulty in swallowing caused by paresis). In these patients, the toxin had been reconstituted in normal saline ($\simeq$100 I.U./ml) without preservative and injected with a 25 or 27 gauge needle. Patients had been evaluated bi-weekly or immediately for evidence of dysphagia. A single treatment consisted of one or more injections to the sternomastoid muscle or to the posterior cervical muscles, or both. The muscles injected had been determined to be dystonic based on palpation, hypertrophy, involuntary spasms, and posture deformity. Each of the 49 injections to the cervical musculature of 26 patients was characterized with respect to dose and injection site. The injections that did not result in dysphagia were then compared with those that did. The data from this retrospective analysis indicated a potential cause-effect relationship between the dysphagia and sternomastoid dosage. Analysis of the data indicated that each patient who experienced dysphagia noted the onset of symptoms within 20 days of the injection and reported a duration of from six days to four weeks. There was no significant difference between total dosage given patients who experienced dysphagia and those who did not. However, if the dose given to individual muscles was evaluated, a significant difference in the dose administered to the sternomastoid muscle was apparent. More specifically, every patient who had experienced dysphagia had had 150 I.U. to 175 I.U. injected into the sternomastoid muscle. In addition to numeric analysis of dose, every patient who experienced dysphagia had been injected in their sternomastoid muscle, and the complication did not occur if the posterior cervical muscle group was alone injected.

Thereafter, 24 patients were enrolled for a prospective study and were asked to report to the investigator promptly should dysphagia occur. Each patient was contacted within four weeks of injection and specifically questioned to assess whether post-injection dysphagia had occurred. Each of these patients were given a dose not greater than 100 I.U. in the sternomastoid muscle at three, four, or five injection points, typically five, of 20 to 35 I.U. per injection site. In addition, eight additional injections were given to six patients who initially experienced dysphagia yet benefited substantially from the previous treatment. Patients from this group were injected after a period of at least five months from the previous injection with a sternomastoid dose of 100 I.U., again in 3 to 5 points along the length of the muscle. None of the next 31 injections in the 24 patients were followed by dysphagia. Furthermore, the six patients previously experiencing dysphagia who received eight injections under the new treatment protocol showed no reoccurrence of dysphagia after 20 weeks follow-up.

These data indicate that injection of 100 to 175 I.U. (2-3 I.U./kg) into the sternomastoid can result in diffusion of the botulinum preparation into deeper muscles of the throat resulting in dysphagia manifest by difficulties in speaking, swallowing, or breathing. In contrast, smaller doses of 20 to 30 I.U. spaced 5-15 mms apart, limiting the total dose to less than about 100 I.U. (<2 I.U./kg) in the sternomastoid resulted in no deep muscle involvement causing dysphagia. In these patients the sternomastoid is about 30 mm from the pharanx.

These data are supported further by the histological observation of strips of obicularis oculi muscle (normally discarded) excised from patients undergoing ptosis surgery who had been treated previously with botulinum A for involuntary blepherospasm, and control specimens of obicularis oculi excised from patients with involutional ptosis who had never been injected with botulinum toxin. The test specimens were obtained four weeks to four months after the last botulinum toxin injection and each was treated to assess denervation as disclosed above. Each toxin treated muscle specimen exhibited extensive spread of acetylcholinesterase activity over the individual muscle fibers. The diffuse pattern of staining, which was associated with muscle fiber atrophy, made identification of discrete neuromuscular junctions difficult. In contrast, each of the four control specimens showed discrete areas of staining on the muscle fiber surface corresponding to acetylcholinesterase activity and position of neuromuscular junctions of the muscle fiber. These and other observations from the clinical treatment of blepharospasm indicate that 20 I.U. botulinum toxin (0.2–0.4 I.U./kg) will spread less than about 30 cm in human obicularis oculi.

In accordance with the invention the toxin may be prepared in dosage form in conventional biologic standardizations such as $LD_{50}$ but most importantly in terms of a unit dose of the toxin's spread capability. This involves nomagram preparation as outlined above and labeling the pharmaceutical agent with the information to provide the physician with the capability of placing injection sites at preselected intervals on the muscle selectively to denervate the muscle and to limit toxin spread in contiguous muscles. This permits expansion of use of the preparations into procedures such as those described below.

Inhibition of Tooth Wear

The involuntary grinding of teetch characteristic of true bruxism is caused by involuntary contractions of the masseter, temporalis and pterygoid muscles. The masseter and temporalis usually are targeted as the muscles which will undergo chemodenervation. They are injected so as to limit the penetration of the toxin to the volume and body of the muscles. Diffusion should be limited to a distance of no more than 25 to 35 mms. A unit dose injection is given at the surface of each of these muscles at multiple points percutaneously or permucosally. Of course, appropriate dental evaluation to assess the degree of damage or potential damage to the teeth should be conducted prior to application of the toxin. The treatment is repeated periodically, e.g., at three to five month intervals as needed to inhibit jaw clenching to protect the teeth, and to relieve the pain syndrome, if any.

Cosmetic Wrinkle Reduction

Facial expression lines such as the transverse forehead lines or the nasolabial fold are created by attachments of projections of facial muscles into the dermis. Contraction of facial muscles generally is well known to produce the various characteristic forms of facial expressions such as smiling, grimacing, etc. In addition, exaggeration of facial lines also is associated with the aging process. The general principle of the application of the toxin is to limit the tonic contractile state of facial muscles so as to reduce muscle tone and to improve or change the quality and characteristics of facial expression.

The transverse forehead lines may be reduced in intensity by injecting a quantity of toxin with a diffusion field of approximately 5 to 10 mms in four injection sites at the superior border of the forehead and at a point approximately 15 mms superior to the brow. This is done symmetrically on both sides of the forehead. The glabellar lines (the frowning lines in the mid position of the forehead) may be targeted by treated the glabellar muscles with a toxin quantity producing a field of denervation of 5 to 10 mms The toxin is injected 15 mms. above the brow line in the mid position of the forehead. The nasal labial fold lines can be diminished in their intensity by treating the zygomatic major and minor muscles which emanate from the zygomatic arch and extend diagonally to the position of the nasal labial fold. An injection of toxin diffusing a distance of 5 to 10 mms over the superior border of these muscles will diminish this line effectively. Furthermore, the position of the lips can be controlled by injecting the zygomatic major and minor muscles. The protrusion of the upper lip can be reduced and even inverted by injection of these muscles. In addition, the protrusion of the lower lip can be reduced by injecting the mentalis muscle at doses producing a denervating field of 5 to 10 mms at the level of the chin approximately 15 mms inferior to the lower lips at a point of approximately 5 mms from the midline.

Stroke and Cerebro-Spinal Injury

Cerebrovascular injuries (stroke and cerebro-spinal injury) can cause spasticity and contractions as a result of paralysis and spasticity. Although the toxin produces a paralysis, it can be useful in reducing muscle mass and in helping spasticity. Symptomatic spasticity can result in chronic involuntary movements as well as difficulties with contracted postures or contractions of the limbs. The application of the drug to these spastic states involves knowledge of innervation zones of limb muscles, (See, e.g., Woolf et al, supra). The muscle which is involved in the abnormal posture or abnormal movement can be identified with an electromyographic needle. Such muscles can also be identified as causing the posture deformities based on experience and an understanding of the muscle's contractile states on the limb position and movement capabilities. These muscles are impaled with a needle at a site close to the innervation zone. In certain situations, it may be necessary to stimulate the muscle with a stimulating current through a teflon coated electromyographic needle to insure the correct placement of the injections. The toxin is injected at a dose level appropriate to create a field of denervation encompassing the innervation zone of the muscle or the entire muscle. Multiple injections over long muscles may be necessary to isolate the effect over that muscle.

Cerebral Palsy

Cerebral palsy results from various forms of brain damage related to anoxia or vascular insufficiency, usually at the time of birth. The destruction of the central cortex of the central motor system results in involuntary movement spasticity, abnormal posturing, and unwanted contractures of muscles. Physical therapy and occassionally antispasmodic drugs are used to treat cerebral palsy. In situations where spasticity is involved with pain, deformity, involuntary movements, or limitations in functional capabilities of a patient, use of the toxin may be indicated. Application involves targeting muscle groups vital to the patient's disability such as muscles which produce limb deformities or impairments in the volitional movements, or in situations where contractures seem to be developing into abnormal postures.

The dosage for treatment of this disease will involve targeting these muscles and using a formulation similar to that used to treat cerebrovascular disease. The prototype for large muscle applications is spasmotic torticollis. The targeted muscles is injected with a dose sufficient to encompass the innervation zone of the muscle.

Multiple Sclerosis

Multiple sclerosis is a disease of white matter of the central nervous system. It involves a demyelination process which leads to impairment of the cortical spinal track and associative tracks in the brain stem. This leads to spinal damage and resultant spasticity. Spasticity in multiple sclerosis can be debilitating because of involuntary movement, contracture, posture deformities, and in certain situations, pain. Use of the toxin is directed and targeted at indications which relieve these particular afflictions relative to the management of the disease.

Again, the toxin is targeted at muscles determined by the physician, neurologist, podiatrist or orthopedic surgeon that appear to be hyperactive. The muscles are injected with a quantity sufficient to encompass volumetrically the muscle or its innervation zone, or both. A working knowledge of muscle anatomy, innervation, and functional anatomy will be needed by the practitioner to achieve optimum results.

Parkinson's Disease

Parkinson's disease is characterized by three basic defects: akinesia (lack of movement); tremor (involuntary movement); and rigidity (increase muscle tone in muscle groups). The toxin can be used to improve the degree of tremor and rigidity present in Parkinson's disease although it probably will be contraindicated in akinesia.

In certain situations in Parkinson's disease, severe dystonias develop in the patient's limbs. In these situations, the involuntary movements are exaggerated, spastic, and often painful. Toxin is injected into the muscle in a dose sufficient to encompass the volume of the muscle or its innervation zone or both. It is done with a stimulating electrode needle to an EMG machine or in conjunction with EMG machine to insure the correct placement of the needle in the muscle. The toxin is given in multiple injection points for large muscles in order to insure an adequate percentage of the innervation zone is encompassed in the injection formulation. The toxin injections must be repeated every three to six months to sustain the desired clinical effect. Total dose administered to initiate a given cycle of denervation—reinnervation should in all cases be far below the $LD_{50}$ for the patient.

The invention may be embodied in other specific forms without departing from the spirit and essential characteristics thereof.

Other embodiments are within the following claims.

What is claimed is:

1. A method of preserving teeth in vivo by decreasing spasm of involuntary contraction in a muscle or group of muscles of a patient induced by pathologic neutral stimulation caused by involuntary jaw clenching, the method comprising:

providing a chemodenervating pharmaceutical characterized in that a unit quantity of said pharmaceutical has been determined to denervate a predetermined volume of said muscle or said group of muscles;

determining a dose of said pharmaceutical required to denervate the predetermined volume of muscle without inducing significant paresis in muscle tissue adjacent said predetermined volume; and injecting a chemodenervating preparation into at least one of the muscles selected from the group consisting of the masseter, temporalis, and pterygoid in an amount sufficient to diminish involuntary jaw clenching while permitting voluntary muscle stimulation, thereby retarding premature tooth wear.

2. A method of decreasing spasm or involuntary contraction in a muscle or group of muscles of a patient induced by pathologic neural stimulation caused by cerebrospinal injury or stroke, the method comprising:

providing a chemodenervating pharmaceutical characterized in that a unit quantity of said pharmaceutical has been determined to denervate a predetermined volume of said muscle or group of muscles;

determining a dose of said pharmaceutical required to denervate the predetermined volume of muscle without inducing significant paresis in muscle tissue adjacent said predetermined volume; and injecting directly into said muscle or muscle group of said patient said dose of said pharmaceutical thereby to decrease the spasm or involuntary contraction in said muscle or muscle group while permitting voluntary muscle stimulation.

3. The method of claim 1 or 2 wherein said denervating preparation comprises a neurotoxin derived from *Clostridium botulinum*.

* * * * *